(12) United States Patent
Cardelius et al.

(10) Patent No.: US 7,127,936 B2
(45) Date of Patent: Oct. 31, 2006

(54) ACOUSTIC ANALYSIS OF GAS MIXTURES

(75) Inventors: Erik Cardelius, Stockholm (SE); Lars Skoglund, Sollentuna (SE)

(73) Assignee: Maquet Critical Care AB, Solna (SE)

( * ) Notice: Subject to any disclaimer, the term of this patent is extended or adjusted under 35 U.S.C. 154(b) by 75 days.

(21) Appl. No.: 10/789,025

(22) Filed: Mar. 1, 2004

(65) Prior Publication Data
US 2004/0200266 A1    Oct. 14, 2004

(30) Foreign Application Priority Data
Mar. 26, 2003   (SE)   ..................... 0300848

(51) Int. Cl.
    *G01N 29/02*  (2006.01)
(52) U.S. Cl. .................... 73/24.01
(58) Field of Classification Search ............ 73/24.01
    See application file for complete search history.

(56) References Cited

U.S. PATENT DOCUMENTS

| | | | |
|---|---|---|---|
| 3,616,677 A * | 11/1971 | Oppegaard | ................. 73/23.21 |
| 4,932,255 A * | 6/1990 | Brace et al. | ............. 73/204.11 |
| 5,141,331 A * | 8/1992 | Oehler et al. | ............... 374/118 |
| 5,247,826 A | 9/1993 | Frola et al. | |
| 5,645,071 A | 7/1997 | Harnoncourt et al. | |
| 6,021,872 A * | 2/2000 | Sevilleja et al. | ............ 187/350 |

FOREIGN PATENT DOCUMENTS

| | | |
|---|---|---|
| EP | 1 336 841 | 8/2003 |
| RU | 1 357 832 | 3/1986 |
| RU | 1 242 726 | 7/1986 |
| WO | WO 92/03724 | 3/1992 |

OTHER PUBLICATIONS

Figliola et al., "Theory and Design for Mechanical Measurements," 1995, John Wiley & Sons, Second Ed., pp. 84-92.*

* cited by examiner

*Primary Examiner*—Daniel S. Larkin
*Assistant Examiner*—John Fitzgerald
(74) *Attorney, Agent, or Firm*—Schiff Hardin LLP

(57) ABSTRACT

An acoustic gas analyzer for gas mixture has an acoustic velocity meter that provides a first output dependent on a detected transmission of acoustic energy through a gas to be analyzed, a temperature probe having a probe time constant that provides a second output indicative of a measured temperature of the gas, and a calculation unit that receives the first and the second outputs and determines compositional information of the gas therefrom. A signal processor is connected between the acoustic velocity meter and the calculation unit and temporally adapts the amplitude of the first output from the meter in a manner dependent on the probe time constant and provides a temporally adapted first output for use as the first output within the calculation unit.

3 Claims, 2 Drawing Sheets

ACOUSTIC ANALYSIS OF GAS MIXTURES

BACKGROUND OF THE INVENTION

1. Field of the Invention

The present invention relates to an acoustic gas analyzer.

2. Description of the Prior Art

In medical and clinical settings it is useful to be able to measure accurately the composition of respiratory (inspiration and/or expiration) gases or changes therein since such measurements can provide, for example, valuable information on patient metabolic conditions. This is particularly the case during the provision of mechanical respiratory aid to a patient where knowledge of the relative and absolute amounts of oxygen and carbon dioxide within the expiration gas may be used to provide information on the metabolization of oxygen as well as respiratory function. Moreover, knowledge of the oxygen/nitrogen ratio in an inspiration gas is useful for controlling or monitoring the provision of respiratory aid using a mechanical breathing aid such as a ventilator, respirator or anesthetic machine.

Gas analyzers are known, for example from WO 92/03724 and from U.S. Pat. No. 5,247,826, for acoustically analyzing the ratios of a mixture of gases comprising two known gases, such as the oxygen/nitrogen ratio in a breathing gas to be supplied to a patient by a mechanical breathing aid. The oxygen concentration or changes therein can then be determined. The known analyzers utilize the physical phenomenon that acoustic waves travel with different velocities through different gases. It is well known that the acoustic velocity, Vg, within a gas mixture can be described by an equation of the form:

$$Vg = \sqrt{C_P \cdot R \cdot Tg / M \cdot C_v} \quad (1)$$

$C_P$ and $C_v$ are the specific heat capacities of the gas mixture at constant pressure and volume respectively; M is the molecular weight of the gas mixture; R is the universal gas constant; and Tg is its absolute temperature. Thus for a gas mixture at a known temperature, Tg, the acoustic velocity, Vg, in the mixture can be used to provide a measure of the relative concentrations of the constituents of the gas.

In general, the known acoustic gas analyzer has an ultrasonic velocity meter with a transducer arrangement that to transmits ultrasound energy along an acoustic path through a gas mixture to be analyzed within a measurement cell or a section of a flow conduit containing the flowing gas mixture and to receive the transmitted energy, a temperature probe disposed to monitor the gas temperature at a point within the cell or section and a calculator for calculating the acoustic velocity Vg of the ultrasound from signals received from the velocity meter and for employing this velocity together with the temperature reading from the probe, in a determination of compositional information for the analyzed gas mixture based on equation (1) above.

In order to determine the instantaneous composition of the gas mixture it is therefore necessary to know simultaneously the temperature of the gas and the acoustic velocity in the gas. It is often the case, however, that the time constant of the temperature probe is long compared with that of the ultrasonic transducer arrangement. The temperature probe may then provide a time-delayed picture of the actual temperature within the gas. This is particularly true where the gas undergoes temperature changes that are more rapid than the time constant of the temperature probe. A simultaneous measurement of the acoustic velocity and the temperature therefore can produce a small temperature error which will result in incorrect compositional information being determined. This can be a problem when the analyzer is employed in the determination of respiratory gas compositional information, since rapid gas pressure changes that normally occur within a ventilator system will result in temperature changes that may be faster than the time constant of the temperature probe.

SUMMARY OF THE INVENTION

It is an object of the present invention to provide an acoustic gas analyzer wherein the above-discussed problems associated with known acoustic gas analyzers are minimized or avoided.

The above object is achieved in accordance with the principles of the present invention in an acoustic gas analyzer having an acoustic velocity meter that provides a first output dependent on detected transmission of acoustic energy through a gas to be analyzed, a temperature probe having a probe time constant and providing a second output indicative of a measured temperature of the gas, and a calculation unit that receives the first and second outputs that determines compositional information of the gas therefrom, and further having a signal processor that temporally adapts the first output dependent on the time constant of the probe so as to provide a temporally-adapted first output that the calculation unit uses as the aforementioned first output, together with the second output, to determine the compositional information.

By temporally adapting the signal provided by the acoustic velocity meter to substantially match that provided by the temperature probe, errors caused by the aforementioned time constant can be considerably reduced.

The signal from the acoustic velocity meter may be passed through a filter designed to subject the velocity related signal to a temporal amplitude variation dependent on the probe time constant.

A recursive filter, for example a digital filter, having characteristics selected to provide the desired temporal variation may be employed as the filter.

DESCRIPTION OF THE PREFERRED EMBODIMENTS

Figure 1:
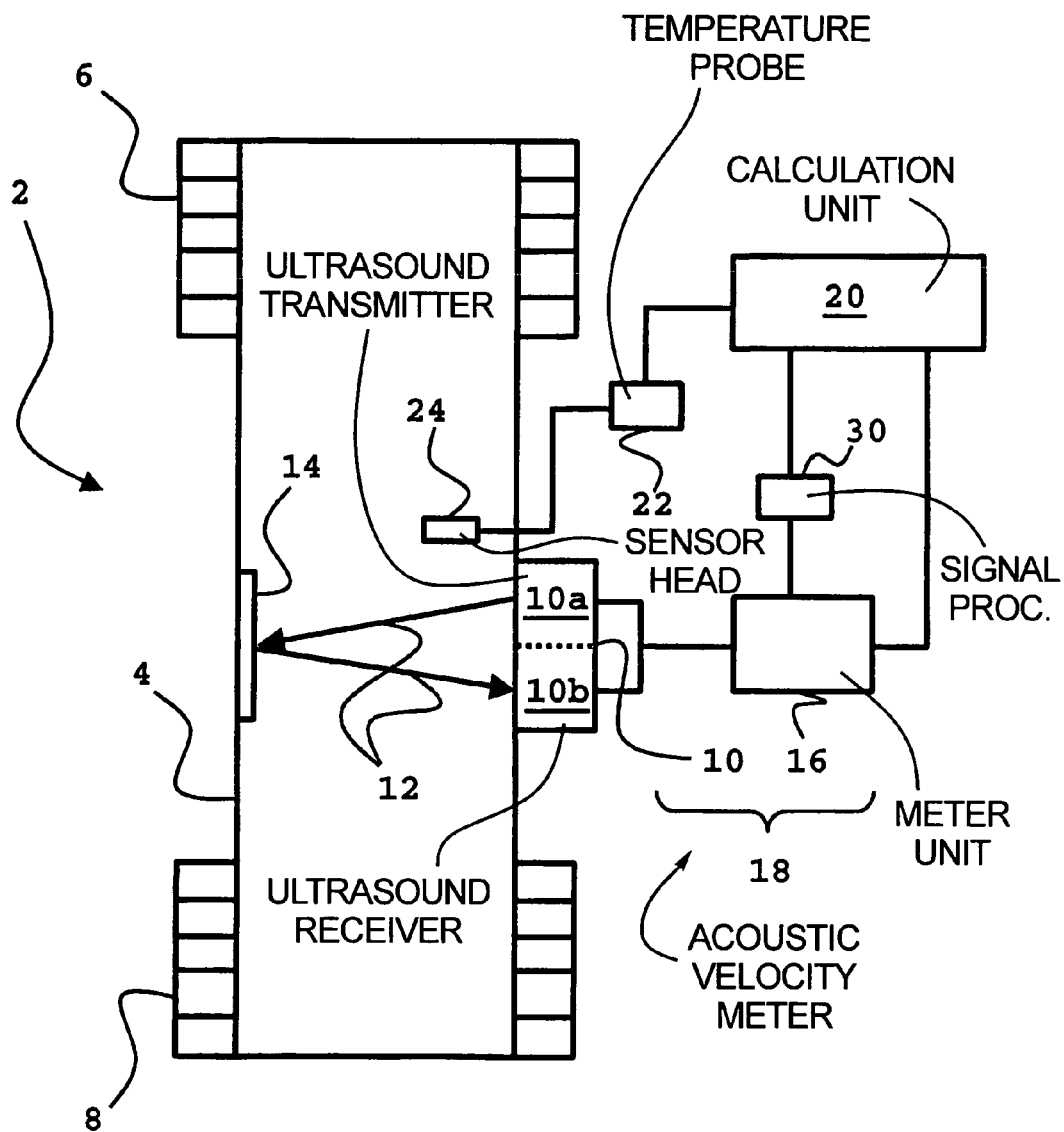
FIG. 1 is a schematic block representation of an exemplary embodiment of an acoustic gas analyzer according to the present invention.

The acoustic gas analyzer 2 represented in FIG. 1 has a gas flow conduit 4 that, as illustrated in the present embodiment, may be a measurement cell having coupling members 6,8 at opposite ends for establishing a releasable connection with an external pneumatic circuit (not shown) of a patient ventilator system, or that may be an integral section of such a pneumatic circuit. An ultrasound transducer arrangement 10 is located with respect to the conduit 4 so as to be able to emit ultrasound energy into and detect the emitted ultrasound after its transmission along a path 12 through a gas to be analyzed within the conduit 4.

In the present embodiment the ultrasound transducer arrangement 10 has a cooperating ultrasound transmitter 10a and receiver 10b located on a same side of the gas flow conduit 4. An ultrasound reflector 14 is also provided in the present embodiment and is disposed generally opposite the transducer arrangement 10 to reflect ultrasound from the transmitter 10a back toward the receiver 10b. It will be appreciated that the ultrasound transducer arrangement 10 can be realized in a large number of different ways while maintaining the basic functionality of emitting ultrasound into and detecting ultrasound transmitted through gas within the conduit 4 and that any one of these ways may be employed within the analyzer 2 without departing from the invention as claimed.

A meter unit 16 is operably connected to the transmitter 10a and receiver 10b to form an acoustic velocity meter 18. The meter unit 16 is configured to operate in the present embodiment in a known manner to control the transmitter 10b to emit a pulse of ultrasound energy at a known time and to measure the time t that the emitted pulse takes to traverse the path 12 through gas within the conduit 4 and to be received at the receiver 10b. In the present embodiment the meter unit 16 is a microprocessor device, which is programmed to determine in a known manner an acoustic velocity V from the time t and a known length L of the path 12 and to provide a first output signal indicative of the determined velocity V. The meter unit 16 is itself connected to a calculation unit 20, such as may be realized by a suitably programmed microcomputer, and which in the present embodiment is further configured to provide command signals to the meter unit 16 to initiate the transmission of the ultrasound pulse at a known sampling rate (typically of the order of a few milliseconds).

A temperature probe 22 is provided as part of the analyzer 2 and has a sensor head 24 disposed to measure temperatures of gas internal of the gas flow conduit 4, preferably proximal or in the acoustic energy transmission path 12. The temperature probe 22 is configured to provide a second output signal to the calculation unit 20 that is indicative of the temperature measured by the head 24. Because the temperature probe 22 has a relatively long measurement time constant the temperature measured by the head 24 may or may not be the actual temperature Tg of the gas within the conduit 4 at which the determination of the acoustic velocity was made. The calculation unit 20 is programmed to utilize in a known manner the temperature measured by the head 24 and the velocity values to determine compositional information about the gas within the conduit 4 based on equation (1) above.

It is well known that the sensor head 24 requires a finite time to equilibrate with its surroundings. The change with time t of the temperature measured by the probe 22 as the head 24 comes into equilibrium has a characteristic form defined by the predetermined probe time constant, as is illustrated by the broken-line temporal response curves 26 in FIGS. 2a and 2b.

Figure 2A:
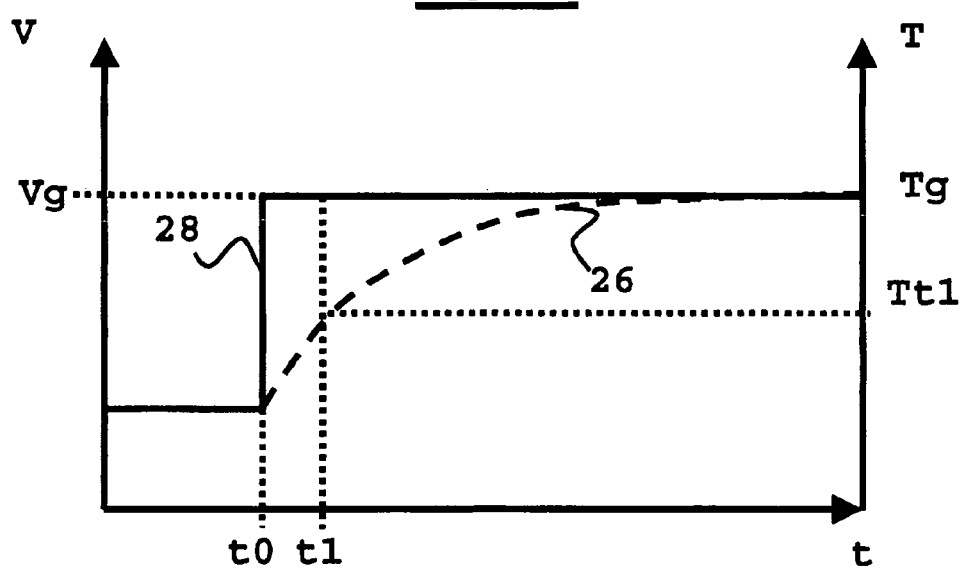
FIGS. 2a and 2b show characteristic temporal response curves for the acoustic velocity meter and the temperature probe of the analyzer of FIG. 1, respectively before adaptation and after adaptation of the output of the velocity meter.
Figure 2B:
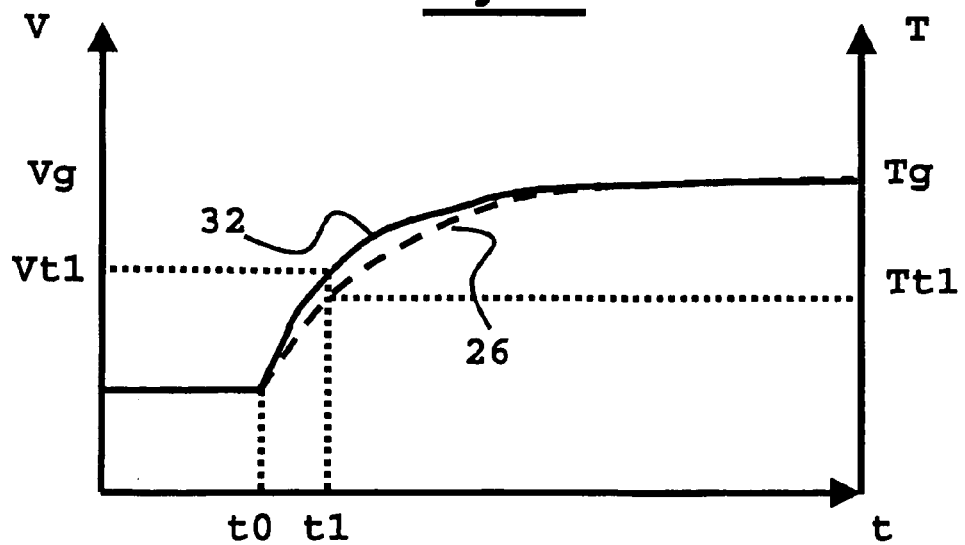

Also shown in FIG. 2a is a characteristic temporal response curve of the acoustic velocity meter 18, which is illustrated by the solid curve 28. As can be seen the acoustic velocity meter 18 responds substantially instantaneously to provide an output being the actual acoustic velocity Vg in the gas within the conduit 4 at the temperature Tg.

The meter unit 16 operates to initiate acoustic velocity measurements at a known sampling rate (represented by the continuation of the solid curve 28 from the time t0) and provides an output, which responds substantially instantaneously to temperature changes (represented by the vertical rising edge of the solid curve 28 at time t0). In the present embodiment the above-mentioned characteristics of the meter unit 16 are exploited to determine a time t0 when a perturbation occurred. To this end the meter unit 16 is further adapted to compare successively measured acoustic velocities for changes in amplitude of a level indicating a temperature change in the gas within the conduit 4. The time t0 therefore can be determined with an accuracy that is dependent on the sampling rate of the velocity meter 18. A signal indicating a detected temperature change is then output from the meter 18.

With reference now to FIG. 2a, generally a determination of compositional information will be made within the calculation unit 20 at a time t1 after a perturbation (t0) in the temperature of gas within the conduit 4 has occurred. Due to the relatively long probe time constant associated with the temperature measurements made by the probe 22, a temperature measurement Tt1, which is passed to the calculation unit 20 at the time t1, will differ from the actual temperature Tg of the gas at that time t1. The manner by which this temperature Tt1 differs is dependent on the probe time constant and has a form shown generally by the broken-line curve 26. A velocity measurement passed to the calculation unit 20 from the velocity meter 18 at the time t1 will be, as mentioned above, a true representation of the velocity Vg of sound in the gas at that time t1.

The time-dependent error in temperature measurement will result in errors in compositional information determined within the calculation unit 20 based on the equation (1). The magnitude of these errors being dependent on the difference between the temperature, Tt1, measured by the sensor head 24 at that time t1 and the actual temperature Tg of the gas.

Returning to FIG. 1, a signal processor 30 is provided as part of the analyzer 2. This is configured to temporally adapt the output from the velocity meter 18 to that output from the temperature probe 22 before it is passed to the calculation unit 20. In the present embodiment the signal processor 30 operates to adapt the measurement signal output from the acoustic velocity meter 18 to mirror the output from the probe 22 and to provide a temporally varying amplitude signal Vt for use within the calculation unit 20 as a measure of the acoustic velocity Vg within the gas in the conduit 4. The adaptation is such that the amplitude of the signal Vt which is output from the processor 30 has a temporal response curve substantially that of the amplitude of the temperature signal from the probe 22. That is, the signal processor 30 operates to make it appear to the calculation unit 20 that the velocity meter 18 reacts as slowly to thermal change as does the temperature probe 22. This is illustrated by the solid curve 32 in FIG. 2(b).

To this end the signal processor 30 can be conveniently configured as a known recursive digital filter 31, having a filter constant K selected to achieve the desired temporal response for the output signal and in the present example operates according to an algorithm of the form:

REPEAT:

$$Vt = Vold*(K-1) + Vg/K$$

$$Vold = Vt$$

UNTIL t=t1 where Vg is the "unfiltered" velocity measured by the acoustic velocity meter 18 at the fixed and known sampling rate. The signal processor 30 is, in the present embodiment, configured to receive the output from the meter 18 which indicates that a perturbation in the temperature of the gas has occurred and which is employed in the processor 30 to initiate (time t0) the filtering of the velocity signal according to the algorithm above.

The constant K may be selected by a repeated comparison of the time dependent form of the output from the signal processor 30 with that from the temperature probe 22 and varying the value of K until a significant match is achieved. This may be done manually or automatically, for example using the calculation unit 20 to perform the comparisons on digital data sets representing the signals from the processor 30 and from the probe 22.

It will be appreciated that while the meter 16, the calculation unit 20, the probe 22 and the processor 30 have all been described as being separate units, some or all of the functionality of some or all of these units may be combined in a suitably programmed microprocessor device fitted with appropriate known interface electronics without departing from the invention as claimed. Moreover, other filter designs, digital or analog, may be provided using known techniques to achieve the generation of a filtered signal having the desired form.

Although other modifications and changes may be suggested by those skilled in the art, it is the intention of the inventors to embody within the patent warranted hereon all changes and modifications as reasonably and properly come within the scope of their contribution to the art.

We claim as our invention:

1. An acoustic gas analyzer comprising:
   an acoustic velocity meter disposed and adapted to interact with a gas to be analyzed by emitting acoustic energy into the gas and detecting said acoustic energy after transmission through the gas, said acoustic velocity meter emitting a first output having an amplitude dependent on the detected transmission of the acoustic energy through the gas at a detection time;
   a temperature probe adapted to interact with the gas to measure a temperature of the gas, and emitting a second output indicative of a measured temperature of the gas, said temperature probe having a probe time constant that causes said measured temperature to represent a temperature of the gas at a time that does not coincide with said detection time;
   a signal processor comprising a filter supplied with said first output for producing a time-dependent variation of the amplitude of said first output, a temporally-adapted first output dependent on the probe time constant that represents a temperature of the gas at the detection time; and
   a calculation unit supplied with said temporally adapted first output and with said second output for determining compositional information of the gas from said temporally-adapted first output and said second output.

2. An acoustic gas analyzer as claimed in claim 1 wherein said filter arrangement comprises a recursive filter having a filter constant that is substantially equal to the probe time constant.

3. An acoustic gas analyzer as claimed in claim 2 wherein said recursive filter is a digital filter.

* * * * *